(12) United States Patent
Yamamoto et al.

(10) Patent No.: US 9,526,562 B2
(45) Date of Patent: Dec. 27, 2016

(54) HIGH-FREQUENCY TREATMENT TOOL

(71) Applicant: OLYMPUS CORPORATION, Tokyo (JP)

(72) Inventors: Tetsuya Yamamoto, Saitama (JP); Fuminori Wake, Kanagawa (JP); Shunsuke Motosugi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/098,447

(22) Filed: Apr. 14, 2016

(65) Prior Publication Data

US 2016/0220301 A1    Aug. 4, 2016

Related U.S. Application Data

(63) Continuation of application No. PCT/JP2015/059951, filed on Mar. 30, 2015.

(30) Foreign Application Priority Data

Aug. 6, 2014  (JP) .................................. 2014-160413

(51) Int. Cl.
*A61B 18/14*    (2006.01)
*A61B 18/12*    (2006.01)
*A61B 18/00*    (2006.01)

(52) U.S. Cl.
CPC ............. *A61B 18/14* (2013.01); *A61B 18/12* (2013.01); *A61B 2018/00083* (2013.01); *A61B 2018/1475* (2013.01); *A61B 2217/007* (2013.01)

(58) Field of Classification Search
CPC ................................ A61B 18/12; A61B 18/14
See application file for complete search history.

(56) References Cited

U.S. PATENT DOCUMENTS 9,237,918 B2 *  1/2016  Yamamoto ....... A61B 17/00234
9,387,034 B2 *  7/2016  Okada .................... A61B 18/14
(Continued)

FOREIGN PATENT DOCUMENTS

EP          2910212 A1     8/2015
JP     2004-313537 A    11/2004
(Continued)

OTHER PUBLICATIONS

International Search Report dated May 12, 2015 issued in PCT/JP2015/059951.

*Primary Examiner* — Michael Peffley
(74) *Attorney, Agent, or Firm* — Scully, Scott, Murphy & Presser, P.C.

(57) ABSTRACT

Provided is a high-frequency treatment tool including a cylindrical sheath, an electrode member that is made to protrude and be retracted with respect to a distal-end portion of the sheath, and a liquid-feeding unit for feeding a liquid toward the distal-end side inside a flow channel in the sheath, wherein a distal end of the electrode member is provided with a distal-end expanded portion that extends radially outward in a radiating manner and that has a base-end surface that is made to protrude and be retracted with respect to a distal-end portion of the sheath, wherein the sheath is provided with a restricting portion that restricts the movement of the electrode member toward the base-end side at a position at which a portion of the distal-end expanded portion is accommodated inside the sheath and an accommodating portion that can accommodate at least a portion of the distal-end expanded portion.

7 Claims, 18 Drawing Sheets

(56) References Cited

U.S. PATENT DOCUMENTS

2004/0210284 A1 10/2004 Okada
2014/0207134 A1* 7/2014 Wake .................. A61B 18/14
　　　　　　　　　　　　　　　　　　　606/39
2014/0288554 A1 9/2014 Okada

FOREIGN PATENT DOCUMENTS

| JP | 2009-112788 A | 5/2009 |
|---|---|---|
| JP | 4315725 B2 | 8/2009 |
| JP | 2012-075657 A | 4/2012 |
| JP | 2013-111308 A | 6/2013 |
| WO | WO 2014/061701 A1 | 4/2014 |

* cited by examiner

HIGH-FREQUENCY TREATMENT TOOL

CROSS-REFERENCE TO RELATED APPLICATIONS

This is a continuation of International Application PCT/JP2015/059951, with an international filing date of Mar. 30, 2015, which is hereby incorporated by reference herein in its entirety.

This application is based on Japanese Patent Application No. 2014-160413, the contents of which are incorporated herein by reference.

TECHNICAL FIELD

The present invention relates to a high-frequency treatment tool.

BACKGROUND ART

In the related art, there is a known high-frequency treatment tool with which biological tissue such as a mucous membrane or the like is treated by applying electricity in the form of a high-frequency current (for example, see Patent Literature 1).

This high-frequency treatment tool has a structure in which an electrode is disposed by being inserted into a sliding hole at the distal end of a flexible sheath having electrically insulating properties so that the electrode can be moved forward and backward in the axial direction, and with which a liquid that has been fed through the flexible sheath can be dispensed from the distal end of the flexible sheath via a liquid-feeding opening portion that communicates with the sliding hole.

With this high-frequency treatment tool, in the case in which bleeding occurs during high-frequency treatment performed by applying electricity to the electrode, washing can be performed by using a liquid, such as physiological saline or the like, dispensed from the distal end of the flexible sheath without having to replace the high-frequency treatment tool, and thus, it is possible to quickly and reliably perform hemostatic treatment for bleeding occurring during an operation. In addition, with this high-frequency treatment tool, because a large-diameter portion provided in the distal end of the electrode is disposed so as to close the liquid-feeding opening portion, the liquid can be released straight ahead by moving the electrode forward to dispose the large-diameter portion away from the liquid-feeding opening portion so that the flow of the liquid is not greatly affected by the large-diameter portion.

CITATION LIST

Patent Literature

{PTL 1} Publication of Japanese Patent No. 4315725

SUMMARY OF INVENTION

Technical Problem

The present invention provides a high-frequency treatment tool with which it is possible to release liquid straight ahead even in a state in which an electrode is retracted.

Solution to Problem

The present invention provides the following solutions.

An aspect of the present invention provides a high-frequency treatment tool including a long, thin cylindrical sheath that is inserted into a body; an electrode member that is disposed so that the electrode member can be freely made to protrude and be retracted with respect to a distal-end portion of the sheath and to which a high-frequency current is supplied; and a liquid-feeding unit for feeding a liquid toward a distal-end side of the sheath from a base-end side thereof inside a flow channel formed along a longitudinal axis of the sheath, wherein a distal end of the electrode member is provided with a distal-end expanded portion that extends radially outward in a radiating manner and that has a base-end surface that is made to protrude and be retracted with respect to the distal-end portion of the sheath, wherein the sheath is provided with a restricting portion that restricts the movement of the electrode member toward the base-end side at a position at which at least a portion of the distal-end expanded portion is accommodated inside the sheath and an accommodating portion having an inner circumferential surface that forms a space in which at least a portion of the distal-end expanded portion can be accommodated inside the sheath, and wherein, at a position at which at least a portion of the distal-end expanded portion is accommodated inside the sheath, the liquid that has been fed via the flow channel collides with a base-end surface of the distal-end expanded portion and is made to flow radially outward; the liquid that has flowed radially outward after colliding with the base-end surface of the distal-end expanded portion collides with the inner circumferential surface of the accommodating portion; and a release port for releasing the liquid is formed between an outer circumferential surface of the distal-end expanded portion and the inner circumferential surface of the accommodating portion.

DESCRIPTION OF EMBODIMENT

A high-frequency treatment tool 1 according to an embodiment of the present invention will be described below with reference to the drawings.

Figure 1:
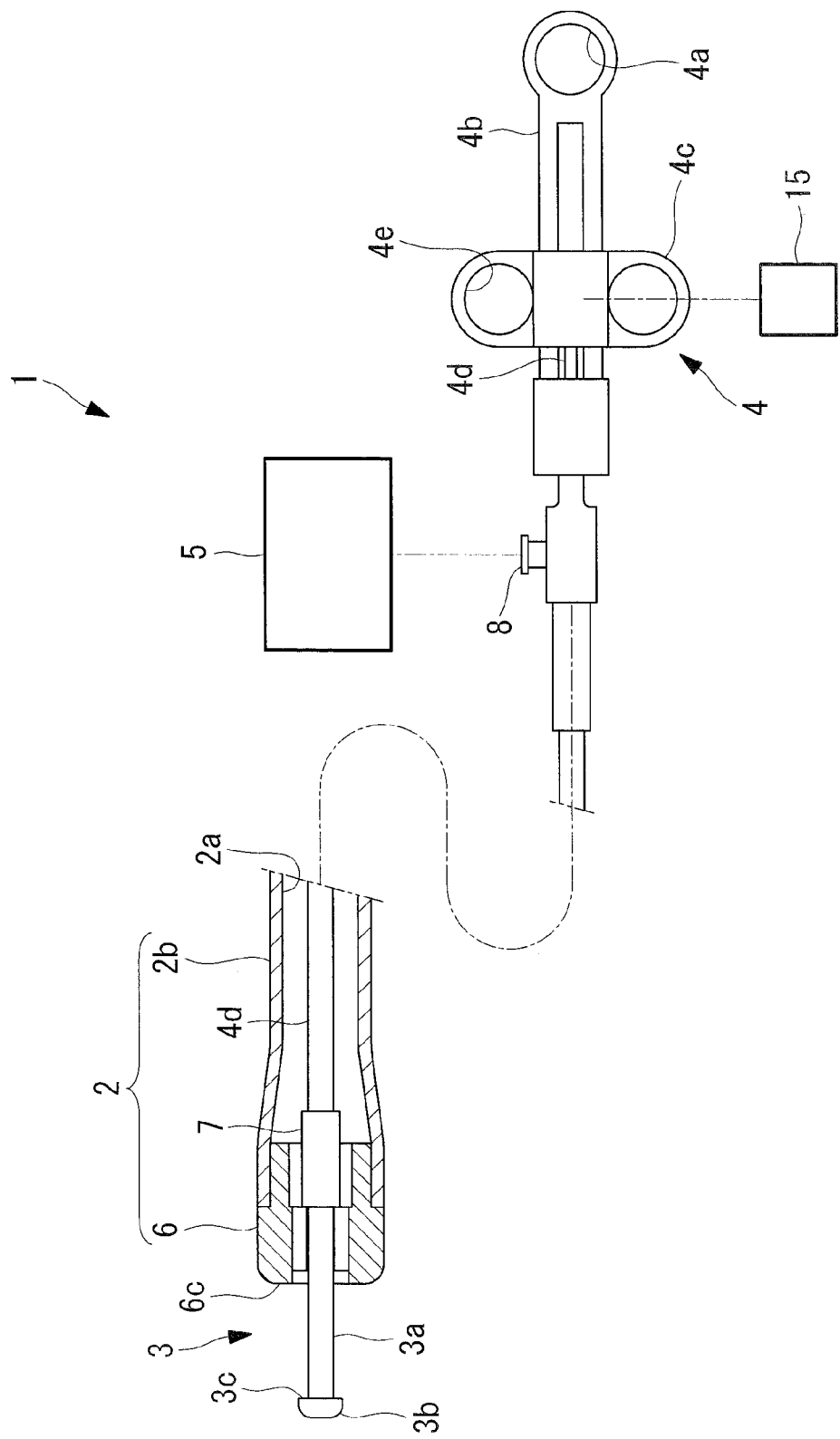
FIG. 1 is an overall configuration diagram showing a high-frequency treatment tool according to an embodiment of the present invention, a portion of which is shown in an enlarged longitudinal sectional view.

As shown in FIG. 1, the high-frequency treatment tool 1 according to this embodiment is, for example, a treatment tool whose distal end is introduced into a body via a channel provided in an inserted portion of an endoscope, and is provided with a sheath 2 that has flexibility and that is formed in a long, thin cylindrical shape which allows insertion thereof into the channel; an electrode member 3 that is advanced and retracted in a distal end of the sheath 2; a manipulation portion 4 that pushes and pulls the electrode member 3 at a base-end side of the sheath 2; and a liquid-feeding unit 5 for dispensing a liquid from the distal end of the sheath 2 via an inner hole 2a of the sheath 2.

Figure 2:
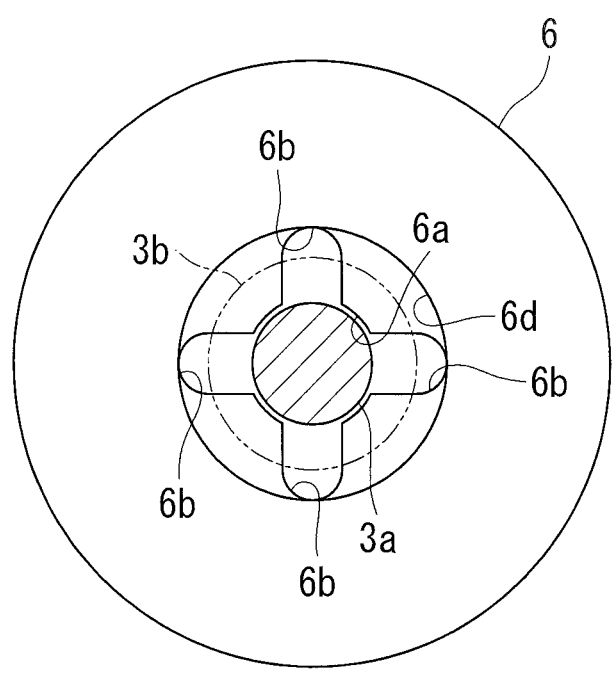
FIG. 2 is a front view of the high-frequency treatment tool in FIG. 1, a portion of which is cut away and which is viewed from the distal-end side of a sheath.

The sheath 2 is constituted of a tube 2b and a distal-end tip 6 that is connected to a distal end of the tube 2b. The distal-end tip 6 is a cylindrical member that is secured so as to be positioned forward relative to the inner hole 2a of the tube 2b. In more detail, in the distal-end tip 6, a distal-end surface in the longitudinal direction is flat, and corners between side surfaces and the distal-end surface have rounded shapes. As shown in FIG. 2, the distal-end tip 6 is provided with a sliding hole 6a to which the electrode member 3 is fitted in a movable manner and one or more, for example, four, grooves 6a in inner surfaces of the sliding hole 6a along the longitudinal direction thereof. In addition, the distal-end surface 6c of the distal-end tip 6 is provided with an accommodating portion 6d, which is depressed one level deeper thereinto. The inner circumferential surface of the accommodating portion 6d is formed in the form of a cylindrical inner surface along the direction substantially parallel to the longitudinal axis of the sheath 2. For example, although the tube 2b and the distal-end tip 6 are formed of an electrically insulating material, the distal-end tip 6 may be formed of a conductive material.

The electrode member 3 is provided with a circular-rod-like columnar portion 3a that has a slightly smaller outer diameter than the inner diameter of the sliding hole 6a of the distal-end tip 6 and a distal-end expanded portion 3b that extends radially outward in a radiating manner over the entire circumference at the distal end of the columnar portion 3a. The distal-end expanded portion 3b is formed in a substantially discoid shape in which the peripheral edge on the distal-end side thereof is rounded. Although the distal-end expanded portion 3b described here is assumed to be formed of a conductive material as with the columnar portion 3a, for example, only the distal-end expanded portion 3b may be formed of an insulating material, such as a ceramic or the like.

Figure 4:
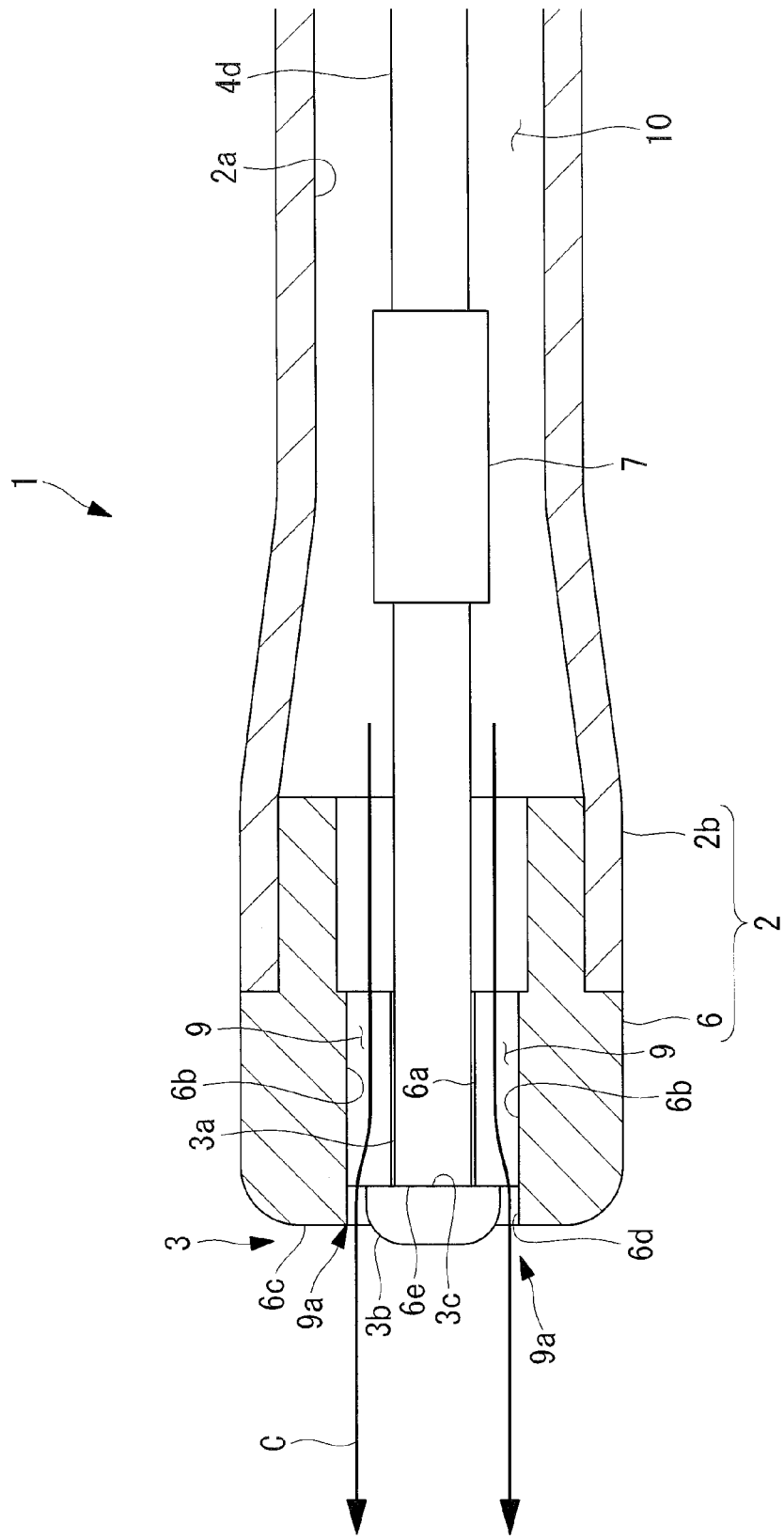
FIG. 4 is a longitudinal sectional view of the vicinity of the distal end of the sheath of the high-frequency treatment tool in FIG. 1.

The outer diameter of the distal-end expanded portion 3b is set to be greater than the diameter of the sliding hole 6a and smaller than the inner diameter of the accommodating portion 6d. In addition, the thickness of the distal-end expanded portion 3b described here is set to be greater than the depth of the accommodating portion 6d, as shown in FIG. 4. By doing so, when the electrode member 3 is retracted, a base-end surface 3c of the distal-end expanded portion 3b is abutted against a bottom surface 6e of the accommodating portion 6d of the distal-end tip 6, thus being locked so as to prevent further retraction, and, in this state, the distal-end expanded portion 3b is disposed so that a portion thereof on the distal-end side is exposed from the accommodating portion 6d. Also, at this time, a release port from which liquid is released is formed between the outer circumferential surface of the distal-end expanded portion 3b and the inner circumferential surface of the accommodating portion 6d.

However, the thickness of the distal-end expanded portion 3b may be set to be nearly the same as the depth of the accommodating portion 6d so that the distal-end surface of the distal-end expanded portion 3b and the distal end of the accommodating portion 6d are positioned on substantially the same plane when the electrode member 3 is retracted.

In addition, as shown in FIG. 2, the outer diameter of the distal-end expanded portion 3b is formed so as to be smaller than the radial-direction size of the grooves 6b formed around the sliding hole 6a. By doing so, when the base-end surface 3c of the distal-end expanded portion 3b is abutted against the bottom surface 6e of the accommodating portion 6d of the distal-end tip 6 by maximally retracting the electrode member 3, portions of the grooves 6b at the radially inner side thereof are closed by the distal-end expanded portion 3b, whereas portions of the grooves 6b at the radially outer side thereof are exposed without being closed.

As shown in FIG. 1, the manipulation portion 4 is provided with a handle 4b that has a finger hole 4a attached to the base-end side of the sheath 2, a movable portion 4c that is provided so as to be movable in the longitudinal axial direction of the sheath 2 with respect to the handle 4b, and a wire 4d that is disposed in the inner hole 2a of the sheath 2 and that links the movable portion 4c and the electrode member 3. Reference sign 4e in the figure indicates finger holes provided in the movable portion 4c.

When the movable portion 4c is moved toward the distal-end side of the sheath 2 relative to the handle 4b, a pressing force is transmitted to the electrode member 3 via the wire 4d, and the electrode member 3 is moved in the direction in which the electrode member 3 is moved forward relative to the distal-end tip 6. In addition, when the movable portion 4c is moved toward the base-end side of the movable portion 4 relative to the handle 4b, a pulling force is transmitted to the electrode member 3 via the wire 4d, and the electrode member 3 is retracted in the direction in which the electrode member 3 is pulled into the sliding hole 6a of the distal-end tip 6. Also, when the movable portion 4c is maximally moved toward the base-end side relative to the handle 4b, the base-end surface 3c of the distal-end expanded portion 3b is locked by abutting against the bottom surface 6e of the accommodating portion 6d so that the movable portion 4c cannot be moved any further.

The wire 4d is connected to the electrode member 3 by means of a conductive stopper portion 7. The stopper portion 7 has a greater outer diameter than the inner diameter of the sliding hole 6a through which the columnar portion 3a of the electrode member 3 passes, and, when the electrode member 3 is moved forward, the electrode member 3 abuts against a level difference formed in an inner side surface of the distal-end tip 6 so as to restrict the amount by which the electrode member 3 protrudes forward. In addition, a power source 15 is connected to the base-end side of the wire 4d so as to supply high-frequency current to the electrode member 3 via the wire 4d.

The handle 4b is provided with a connecting port 8 that communicates with the inner hole 2a of the sheath 2.

The liquid-feeding unit 5 is a syringe, a liquid-feeding pump, or the like that is connected to the connecting port 8, and a liquid C, such as physiological saline, is fed into the inner hole 2a of the sheath 2 by activating the liquid-feeding unit 5.

In this embodiment, in the state in which the electrode member 3 is fitted into the sliding hole 6a, the grooves 6b at the four locations form four flow channels 9 that are roughly divided by the columnar portion 3a of the electrode member 3. The four flow channels 9 are disposed in the circumferential direction of the columnar portion 3a with spaces therebetween, and individually have cylindrical flow channels 10 that are formed between the inner hole 2a of the sheath 2 and the wire 4d and that open forward at the distal-end tip 6. In other words, the four flow channels 9 individually open into a ring-shaped space between the accommodating portion 6d of the distal-end tip 6 and the distal-end expanded portion 3b.

Figure 3:
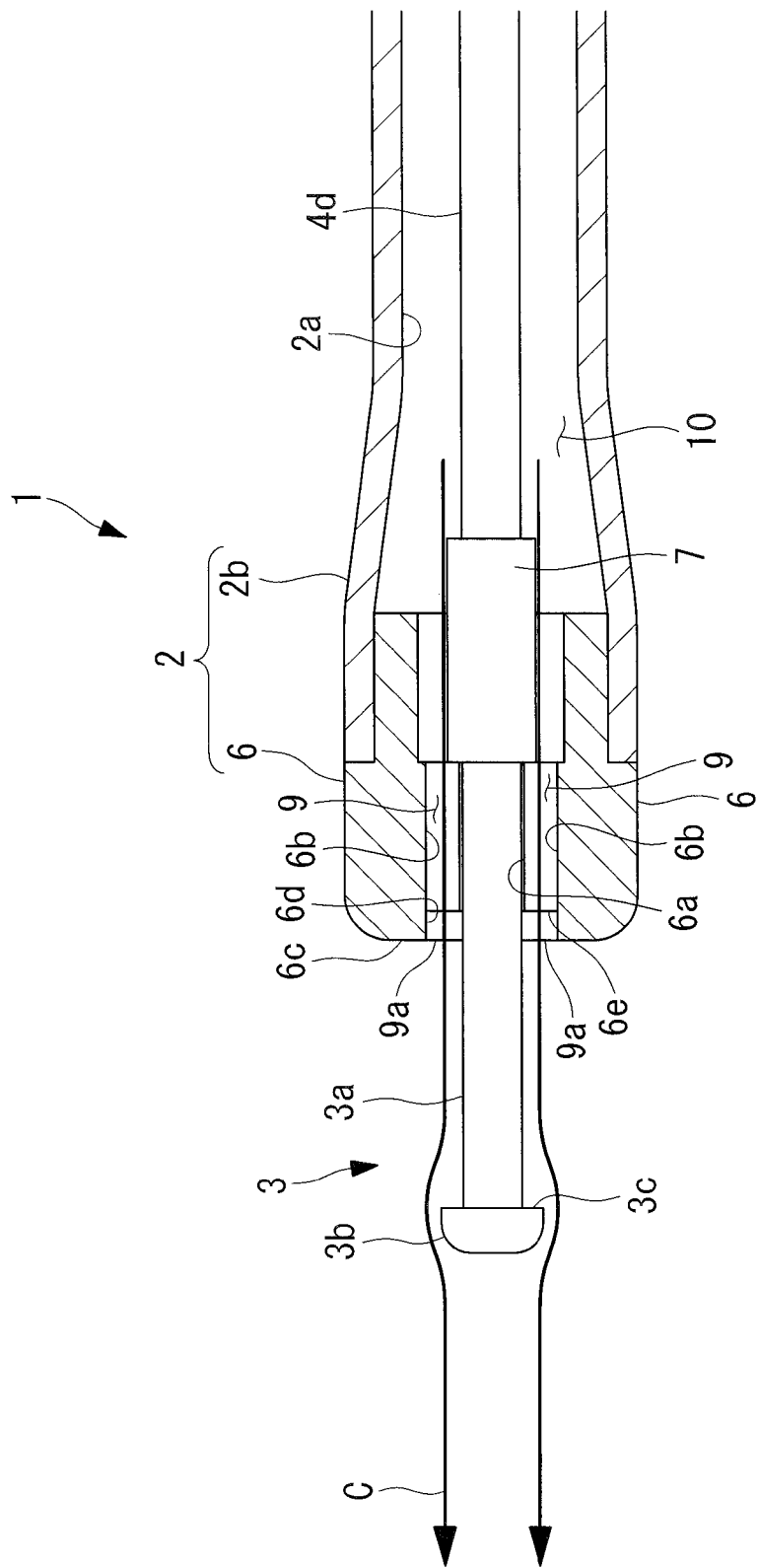
FIG. 3 is a longitudinal sectional view of the vicinity of the distal end of the sheath in the state in which an electrode member of the high-frequency treatment tool in FIG. 1 is moved forward.

Thus, openings 9a of the individual flow channels 9 are configured so that most of the liquid C dispensed from the openings 9a is released straight ahead in the direction extended from the longitudinal axis of the sheath 2 beyond the distal-end expanded portion 3b when the electrode member 3 is moved forward and the distal-end expanded portion 3b is separated from the distal-end tip 6 in the forward direction, as shown in FIG. 3. On the other hand, when the electrode member 3 is retracted and the distal-end expanded portion 3b is accommodated in the accommodating portion 6d of the distal-end tip 6, as shown in FIG. 4, the liquid C that has flowed inside the flow channels 9 collides with the distal-end expanded portion 3b, which partially closes the openings 9a of the flow channels 9, and, although this temporarily directs the liquid C radially outward, the inner circumferential surface of the accommodating portion 6d directs the liquid C in the direction along the longitudinal axis of the sheath 2 again.

The operation of the thus-configured high-frequency treatment tool 1 according to this embodiment will be described below.

In order to perform endoscopic submucosal dissection by using the high-frequency treatment tool 1 according to this embodiment, the manipulation portion 4 is manipulated to introduce the sheath 2 into the body from the distal-end side thereof via the channel in the inserted portion of the endoscope in the state in which the electrode member 3 is maximally retracted, and thus, the distal end of the sheath 2 is made to protrude from the distal end of the inserted portion of the endoscope.

By doing so, because the distal end of the sheath 2 is brought into the viewing field of the endoscope, an operator performs treatment while checking an image acquired by the endoscope on a monitor. In the state in which the electrode member 3 is maximally retracted, because only the distal-end portion of the distal-end expanded portion 3b is exposed forward from the distal-end tip 6, tissue is not deeply cut into even if a high-frequency current is applied to the electrode member 3 in this state, and it is possible to perform so-called marking in which only the tissue surface is cauterized.

In other words, the operator can form a mark that surrounds an area surrounding the site of a lesion-to-be-removed by applying electricity while pressing the distal-end surface 6c of the distal-end tip 6 against multiple locations that surround a site suspected to be a lesion-to-be-removed in an endoscope image displayed on the monitor, and he/she can use the mark as a guide for the subsequent treatment.

Subsequently, the electrode member 3 is made to protrude from the distal-end surface 6c of the distal-end tip 6 by manipulating the manipulation portion 4, and an incision is made in tissue by applying the high-frequency current thereto. Next, the electrode member 3 is maximally retracted by manipulating the manipulation portion 4, and the distal-end tip 6 pierces into the submucosa below the lesion site. Then, the liquid-feeding unit 5 is activated to dispense the liquid C from the openings 9a at the distal-end surface 6c of the distal-end tip 6. By doing so, the liquid C is locally injected into the submucosa, thus raising the lesion site.

In this state, the sheath 2 is removed from the submucosa, the electrode member 3 is made to protrude again by manipulating the manipulation portion 4, and an incision is made in the tissue surrounding the lesion site by using the mark formed by marking as a guide.

In the case in which bleeding occurs while making the incision, the bleeding area can be washed by activating the liquid-feeding unit 5 to dispense the liquid C from the openings 9a at the distal-end surface 6c of the distal-end tip 6.

In this case, when the electrode member 3 is moved forward and the liquid C is released in the state in which the distal-end expanded portion 3b is separated from the distal-end surface 6c of the distal-end tip 6, nearly all of the liquid C dispensed from the openings 9a of the flow channels 9 of the distal-end tip 6 is released forward beyond the distal-end expanded portion 3b. Therefore, because the liquid C is released in the direction in which the distal end of the sheath 2 displayed in the endoscope image is directed, it is easy to aim at the position to which the liquid C is to be applied, and thus, it is possible to quickly wash the bleeding area in the aimed-at location.

In addition, in some cases, hemostatic treatment is performed by cauterizing the bleeding location by means of a high-frequency current after washing the bleeding area. When performing this hemostatic treatment, cauterization is performed by maximally retracting the electrode member 3, as with when performing marking. Therefore, it is more preferable to release the liquid C in a state in which the electrode member 3 is maximally retracted in advance to wash the aimed location, and to quickly perform the hemostatic work without interruption.

In the case in which washing is performed in the state in which the electrode member 3 is maximally retracted, the distal-end expanded portion 3b is accommodated in the accommodating portion 6d, and thus, the openings 9a of the flow channels 9 formed in the bottom surface 6a of the accommodating portion 6d are partially closed by the distal-end expanded portion 3b.

Therefore, the liquid C that has flowed via the flow channels 9 is blocked by the distal-end expanded portion 3b, the flow direction thereof is temporarily directed radially outward to be released into the accommodating portion 6d, and the liquid C is released forward from the sheath 2 through a ring-shaped gap between an inner wall of the accommodating portion 6d and the outer circumference of the distal-end expanded portion 3b. In this case, because the inner wall of the accommodating portion 6d and the outer circumference of the distal-end expanded portion 3b are formed so as to be parallel to the longitudinal axis of the sheath 2, the liquid C is released after the flow direction thereof is returned to the direction along the inner wall of the accommodating portion 6d and the outer circumference of the distal-end expanded portion 3b, that is, the longitudinal axial direction.

As a result, with the high-frequency treatment tool 1 according to this embodiment, there is an advantage in that, also in the state in which the electrode member 3 is maximally retracted, it is possible to release the liquid C into the direction in which the distal end of the sheath 2 is directed, it is easy to aim at the position to which the liquid C is to be applied, and it is possible to quickly wash the bleeding area in the aimed-at location. In other words, because the liquid C is released straight ahead even in the state in which the electrode member 3 is not protruded, it is possible to prevent the electrode member 3 from becoming a hindrance by coming into contact with tissue in the surrounding area or the like during a washing operation performed while moving the sheath 2.

Note that, in the case in which a lesion portion starts to drop down when the liquid C locally injected into the submucosa is absorbed into another site or the like in the process of making an incision in tissue in the surrounding area of an affected portion, the liquid C is locally injected by pressing the distal-end tip 6 against the submucosa again. In this case also, by dispensing the liquid C by maximally retracting the electrode member 3, it is possible to perform local injection while preventing the electrode member 3 from piercing into the tissue more than necessary.

Figure 15A:
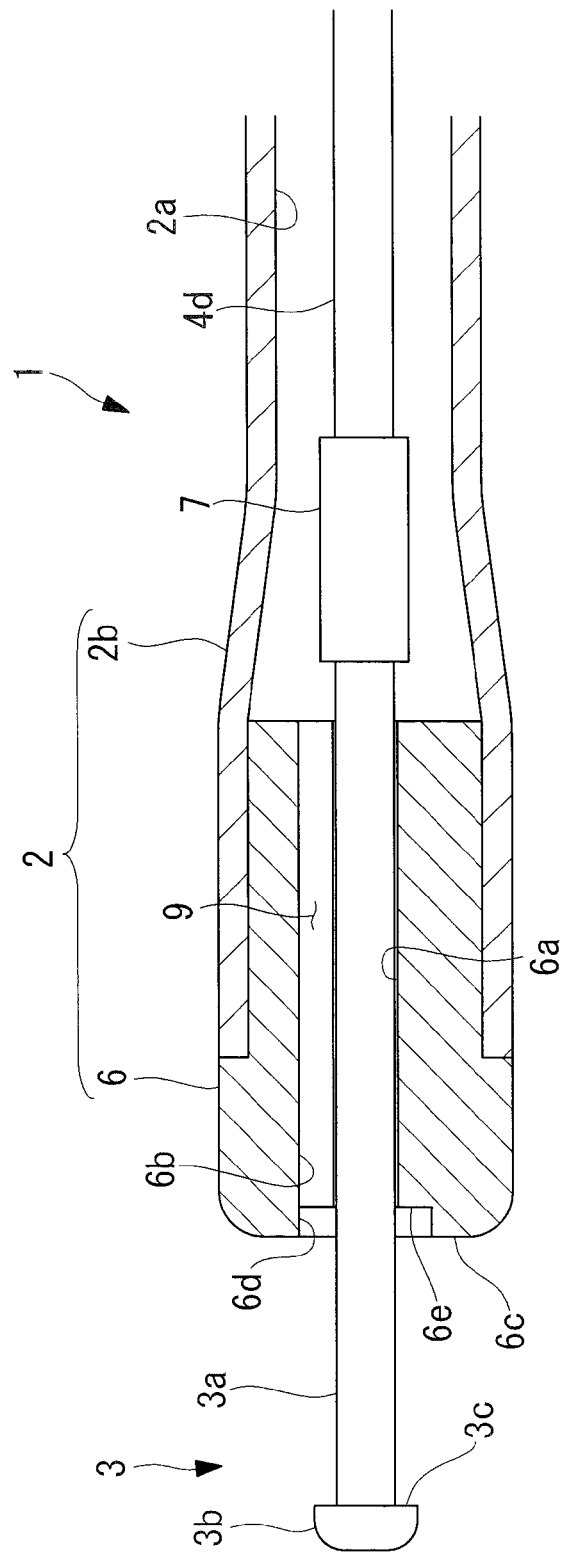
FIG. 15A is a longitudinal sectional view of the vicinity of the distal end of the sheath showing a tenth modification of the high-frequency treatment tool in FIG. 1 in the state in which the electrode member is moved forward.
Figure 15B:
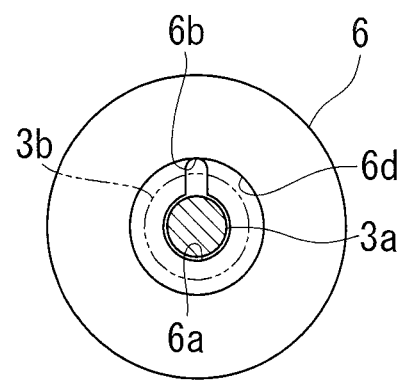
FIG. 15B is a front view of the vicinity of the distal end of the sheath showing the tenth modification of the high-frequency treatment tool in FIG. 1 in the state in which the electrode member is moved forward.
Figure 15C:
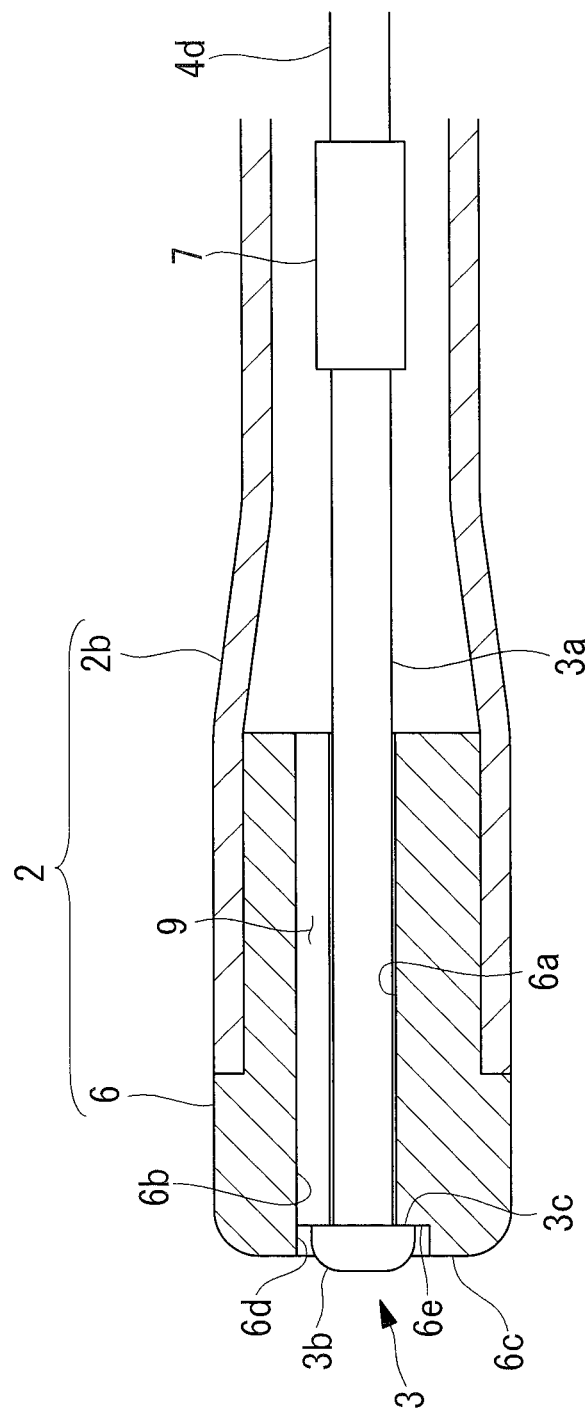
FIG. 15C is a longitudinal sectional view of the vicinity of the distal end of the sheath showing the tenth modification of the high-frequency treatment tool in FIG. 1 in the state in which the electrode member is retracted.

In addition, in this embodiment, the four grooves 6b are provided around the sliding hole 6a, and the four flow channels 9 that are divided by the columnar portion 3a of the electrode member 3 fitted to the sliding hole 6a are formed; alternatively, however, the grooves 6b may be formed in an arbitrary number equal to or greater than one. In addition, although the grooves 6b are provided in the circumferential direction with equal spaces therebetween, they may be provided with unequal spaces therebetween. FIGS. 15A to 15C show cases in which a single groove 6b is provided.

Figure 5:
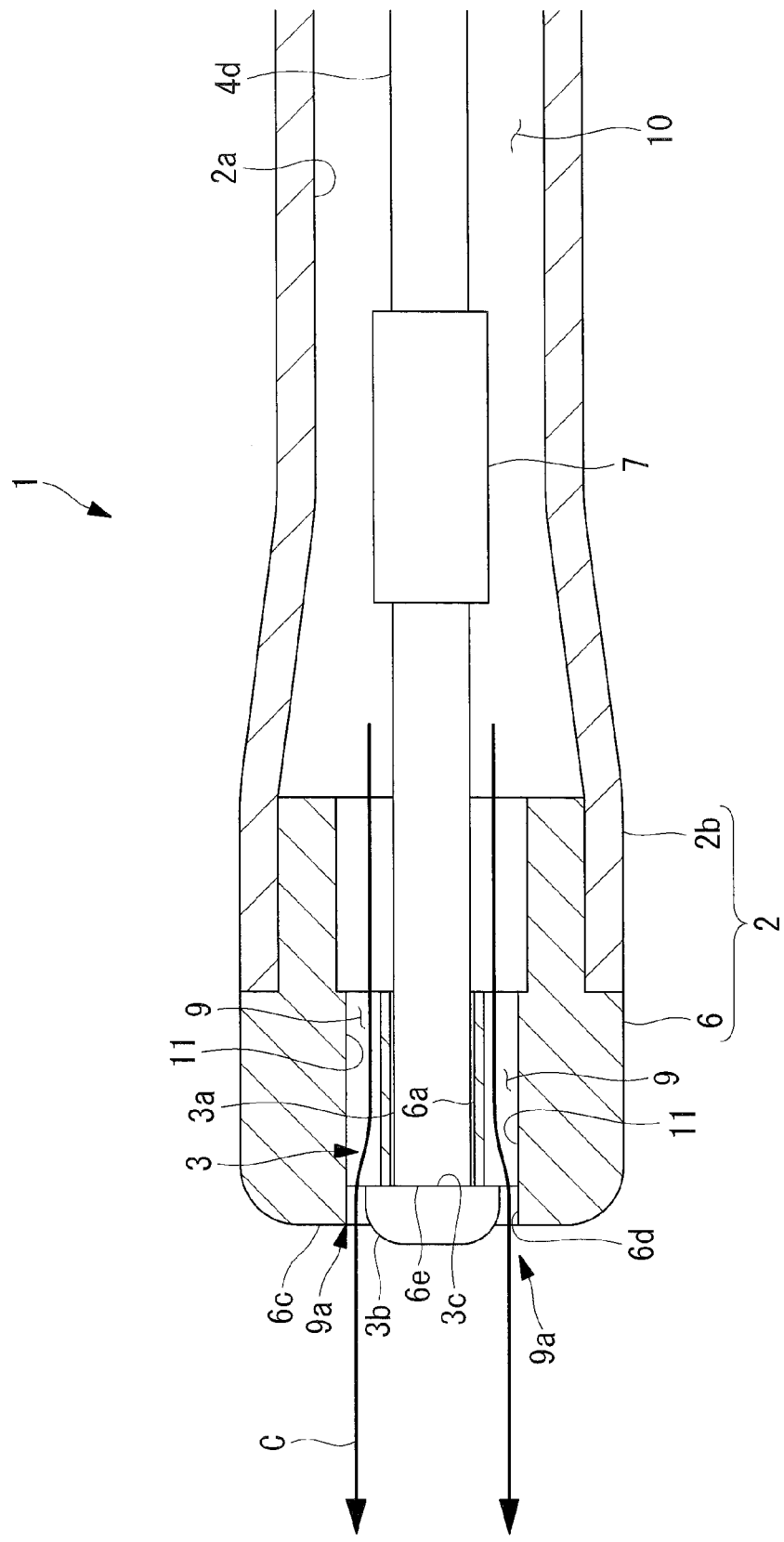
FIG. 5 is a longitudinal sectional view of the vicinity of the distal end of the sheath showing a first modification of the high-frequency treatment tool in FIG. 1.

In addition, although the flow channels 9 are formed by the grooves 6b connected to the sliding hole 6a, the sliding hole 6a to which the electrode member 3 is fitted in a movable manner and the flow channels 9 in which the liquid C flows may be formed independently of each other. In this case, a plurality of through-holes 11 should be formed so as to be parallel to the sliding hole 6a, as shown in FIG. 5. In addition, although the cylindrical flow channels 10 are formed between the inner surface of the inner hole 2a of the sheath 2 and the wire 4d, inner holes (not shown) that form the flow channels 10 independently of the inner hole 2a in which the wire 4d is disposed may be provided.

Figure 6:
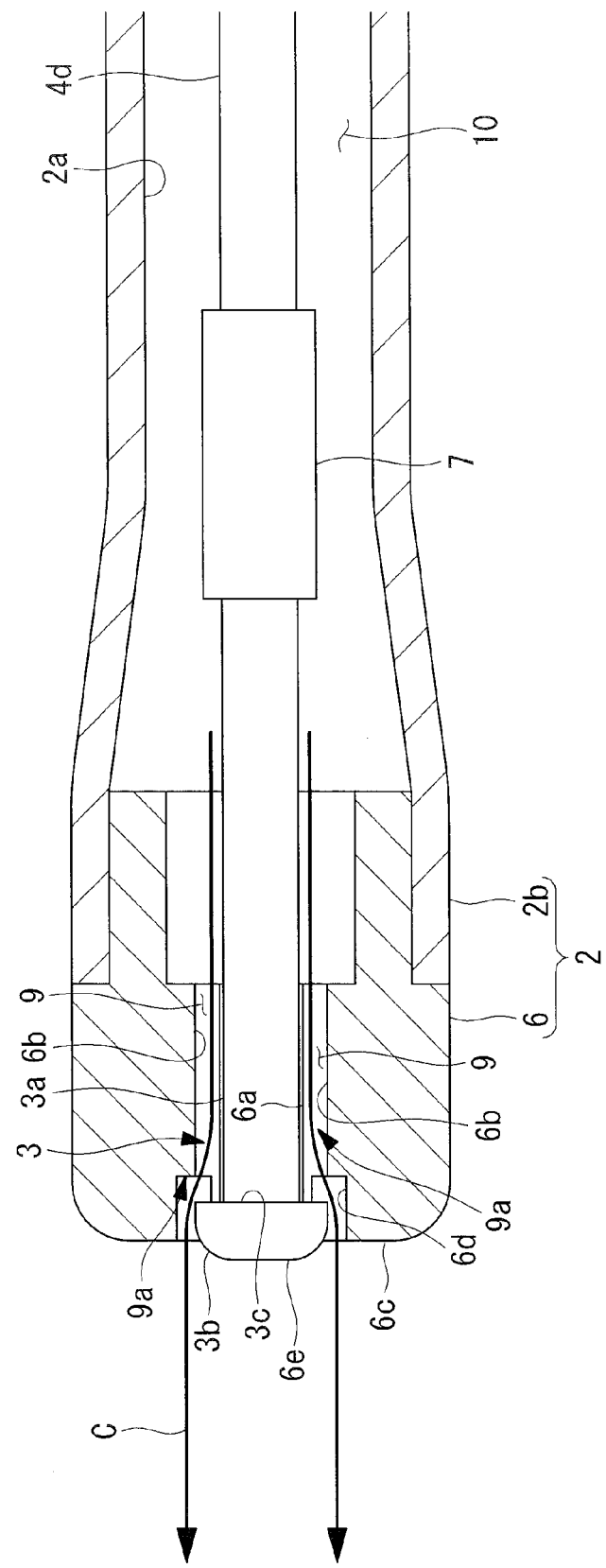
FIG. 6 is a longitudinal sectional view of the vicinity of the distal end of the sheath showing a second modification of the high-frequency treatment tool in FIG. 1.
Figure 7:
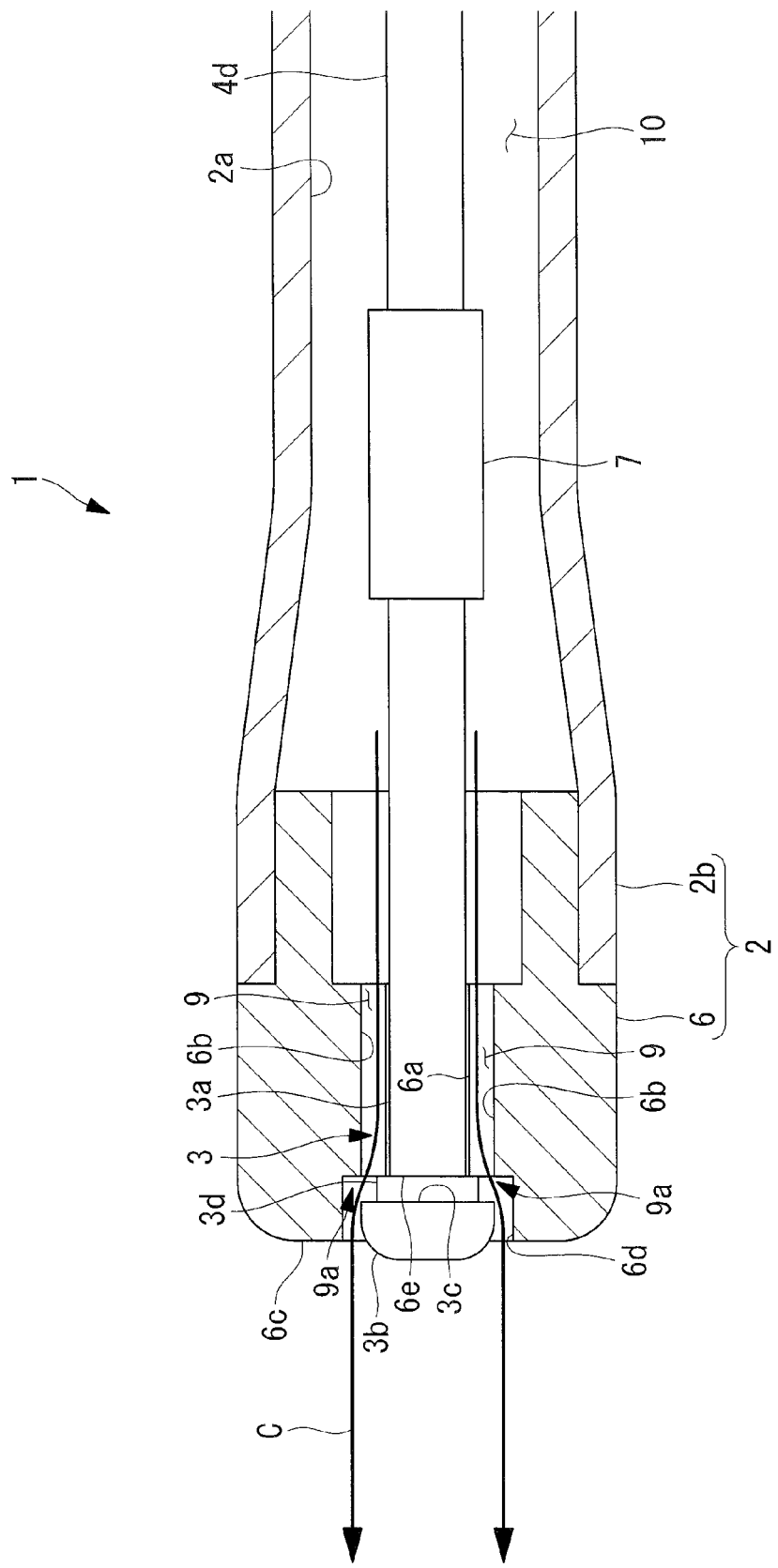
FIG. 7 is a longitudinal sectional view of the vicinity of the distal end of the sheath showing a third modification of the high-frequency treatment tool in FIG. 1.

In addition, in this embodiment, in order to partially close the openings 9a of the flow channels 9 by using the maximally retracted distal-end expanded portion 3b, the openings 9a of the flow channels 9 are formed so as to protrude radially farther outward than the outer diameter of the distal-end expanded portion 3b; alternatively, however, it is permissible not to make the openings 9a of the flow channels 9 protrude radially outward. In other words, by making the bottom surface 6e of the accommodating portion 6d, which makes the distal-end expanded portion 3b abut against the distal-end tip 6, protrude slightly farther forward than the openings 9a of the flow channels 9, as shown in FIG. 6, or by providing a level difference 3d or an inclined surface 3e in the base-end surface 3c of the distal-end expanded portion 3b, as shown in FIGS. 7 and 8, the openings 9a of the flow channels 9 may be partially opened even in the state in which the distal-end expanded portion 3b is abutted against the bottom surface 6e.

Figure 9:
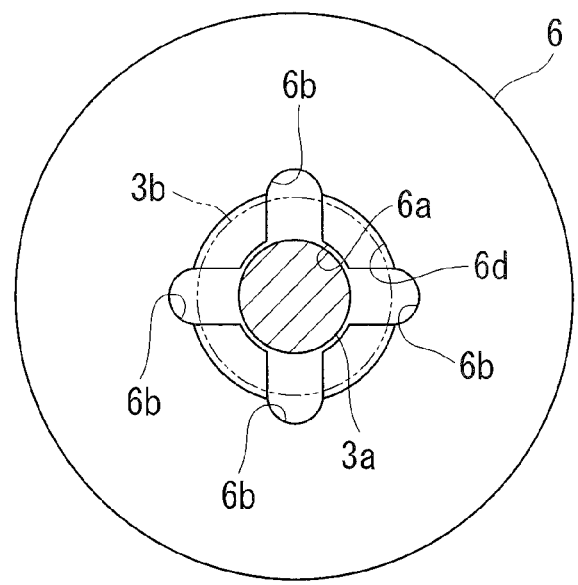
FIG. 9 is a front view of a fifth modification of the high-frequency treatment tool in FIG. 1, a portion of which is cut away and which is viewed from the distal-end side of the sheath.

In addition, in this embodiment, the openings 9a of the flow channels 9 are provided at the bottom surface 6e of the accommodating portion 6d. By doing so, because the liquid C released from the openings 9a of the flow channels 9 is dispensed from nearly the entire circumference of the accommodating portion 6d, there is an advantage in that the amount to be dispensed can be increased due to the flow having a substantially ring-like lateral cross-sectional shape. Alternatively, as shown in FIG. 9, by making the size of the accommodating portion 6d close to the outer diameter of the distal-end expanded portion 3b, the grooves 6b may be protruded radially farther outward than the inner surface of the accommodating portion 6d. By doing so, because the liquid C is dispensed mainly from the flow channels 9 formed by the grooves 6b, the liquid C can be released in the form of a converged narrow flow.

Figure 10:
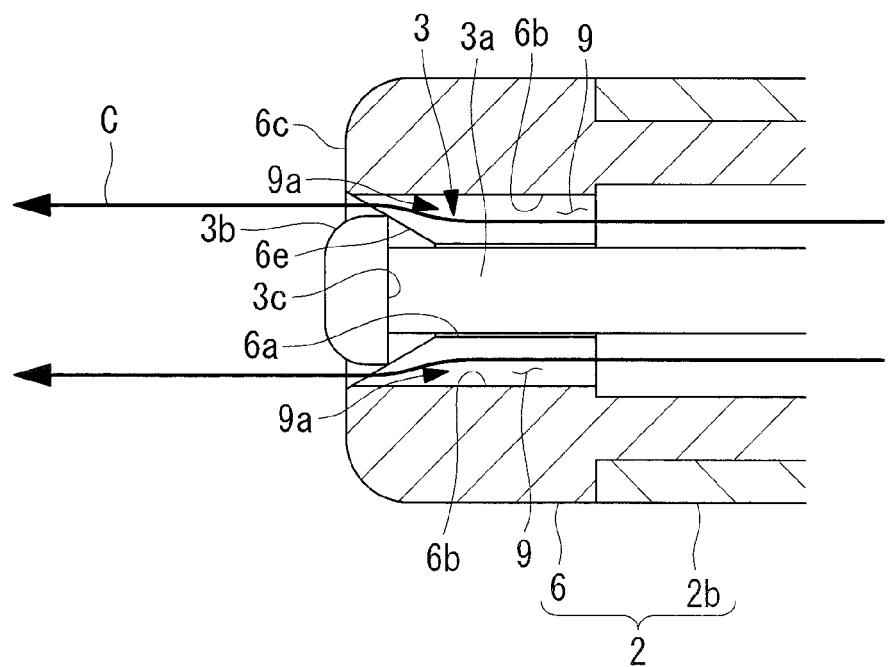
FIG. 10 is a longitudinal sectional view of the vicinity of the distal end of the sheath showing a sixth modification of the high-frequency treatment tool in FIG. 1.

In addition, in this embodiment, although the base-end surface 3c of the discoid distal-end expanded portion 3b is abutted, in surface contact, against the bottom surface 6e of the accommodating portion 6d, alternatively, as shown in FIG. 10, by forming the bottom surface 6e of the accommodating portion 6d as a tapered inner surface, the base-end surface 3c of the distal-end expanded portion 3b may be abutted in line contact. By doing so, when the discoid distal-end expanded portion 3b is abutted against the bottom surface 6e of the accommodating portion 6d, it is possible to coaxially dispose (center) the electrode member 3 with the sliding hole 6a, and it is possible to prevent bias in the circumferential direction of the dispensed liquid C.

Figure 8:
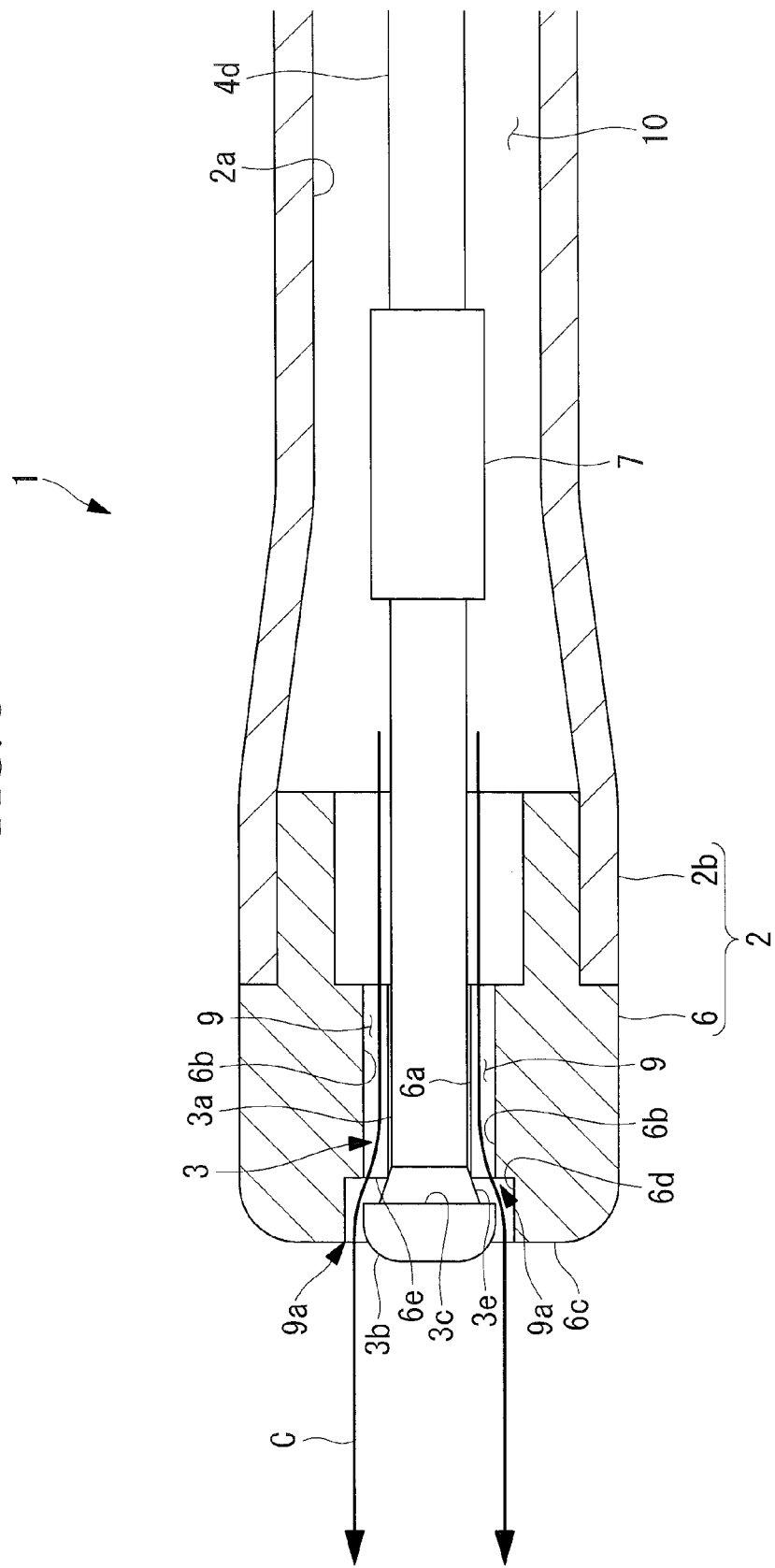
FIG. 8 is a longitudinal sectional view of the vicinity of the distal end of the sheath showing a fourth modification of the high-frequency treatment tool in FIG. 1.

In addition, although the arrangements are opposite to those described above, it is possible to achieve similar operational effects by providing, as shown in FIG. 8, a tapered inclined surface 3e in a back surface 3c of the substantially discoid distal-end expanded portion 3b and by abutting, in line contact, the back surface 3c against the opening on the distal-end side of the sliding hole 6a.

Figure 11:
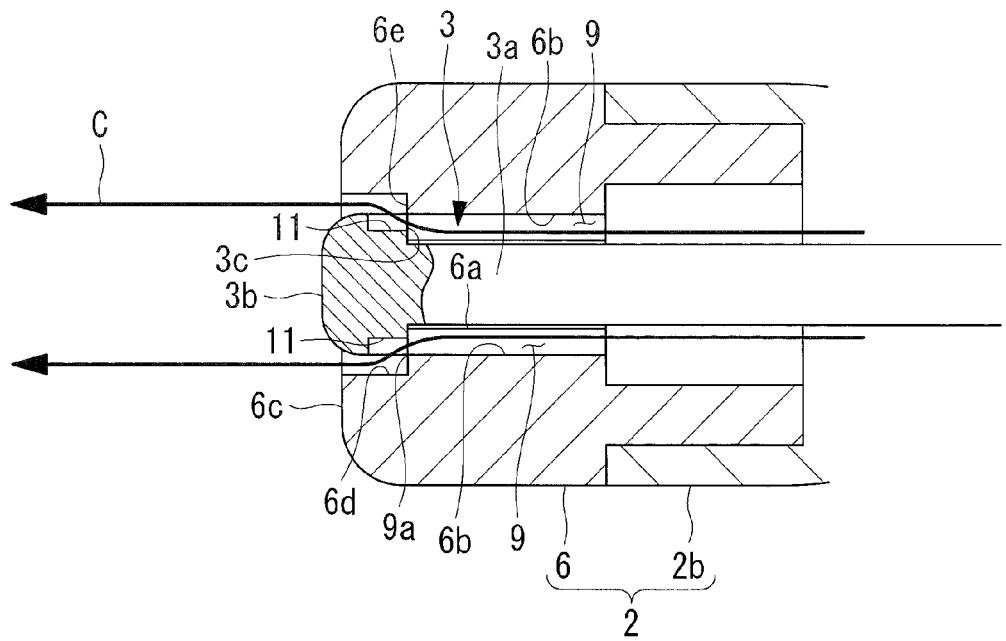
FIG. 11 is a longitudinal sectional view of the vicinity of the distal end of the sheath showing a seventh modification of the high-frequency treatment tool in FIG. 1.
Figure 12:
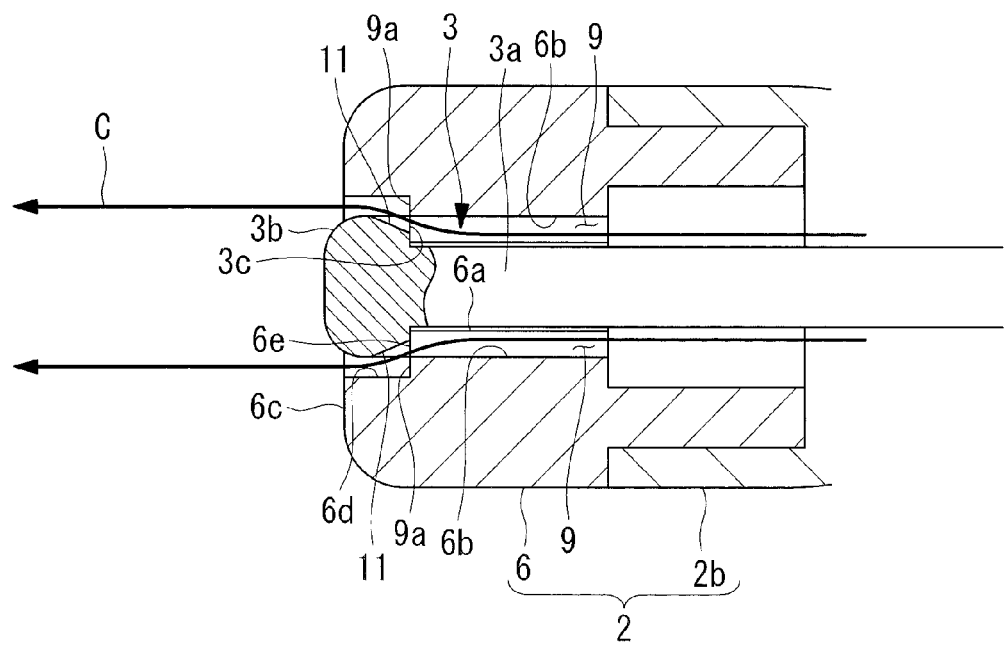
FIG. 12 is a longitudinal sectional view of the vicinity of the distal end of the sheath showing an eighth modification of the high-frequency treatment tool in FIG. 1.

In addition, as shown in FIGS. 11 and 12, the base-end surface 3c of the substantially discoid distal-end expanded portion 3b may be provided with one or more notch-like groove portions 11 that extend to intermediate positions in the longitudinal axial direction. The flow direction of the liquid C that has entered the groove portions 11 from the flow channels 9 is changed to the radially outward direction, the flow direction thereof is subsequently corrected to the longitudinal axial direction again by the inner circumferential surface of the accommodating portion 6d in the surrounding area, and thus, the liquid C is dispensed forward in the longitudinal axial direction. There is an advantage in that the amount to be dispensed can be increased by using the groove portions 11.

The number of the groove portions 11 may be an arbitrary number so long as it is equal to or greater than one. In addition, the groove portions 11 may be level differences, as shown in FIG. 11, or the groove portions 11 may be inclined surfaces, as shown in FIG. 12. In addition, the width of the groove portions 11 may be narrow or wide. In addition, the groove portions 11 may be provided in the circumferential direction with equal spaces therebetween, or the groove portions 11 may be provided with unequal spaces therebetween. In addition, it is permissible to make the width and the shape of the groove portions 11 non-uniform.

Figure 13:
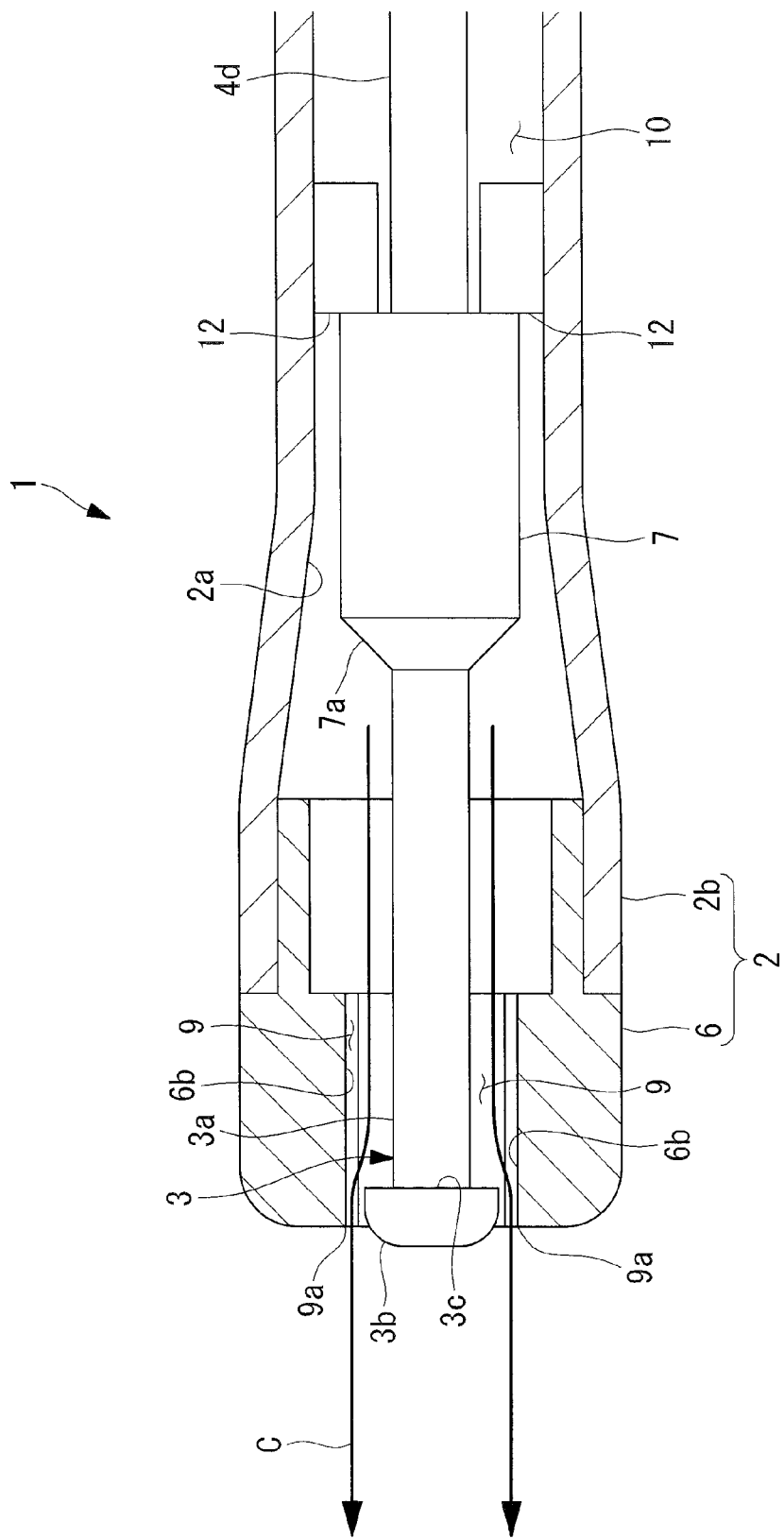
FIG. 13 is a longitudinal sectional view of the vicinity of the distal end of the sheath showing a ninth modification of the high-frequency treatment tool in FIG. 1.

In addition, in this embodiment, although the base-end surface 3c of the discoid distal-end expanded portion 3b is abutted against the bottom surface 6e of the accommodating portion 6d, alternatively, as shown in FIG. 13, an abutting surface 12 against which a step portion on the base-end side of a stopper portion 7 is abutted may be provided. In this case, a plurality of the abutting surfaces 12 should be provided in the circumferential direction with spaces therebetween, and the flow channels 9 should be formed between the abutting surfaces 12.

Figure 14:
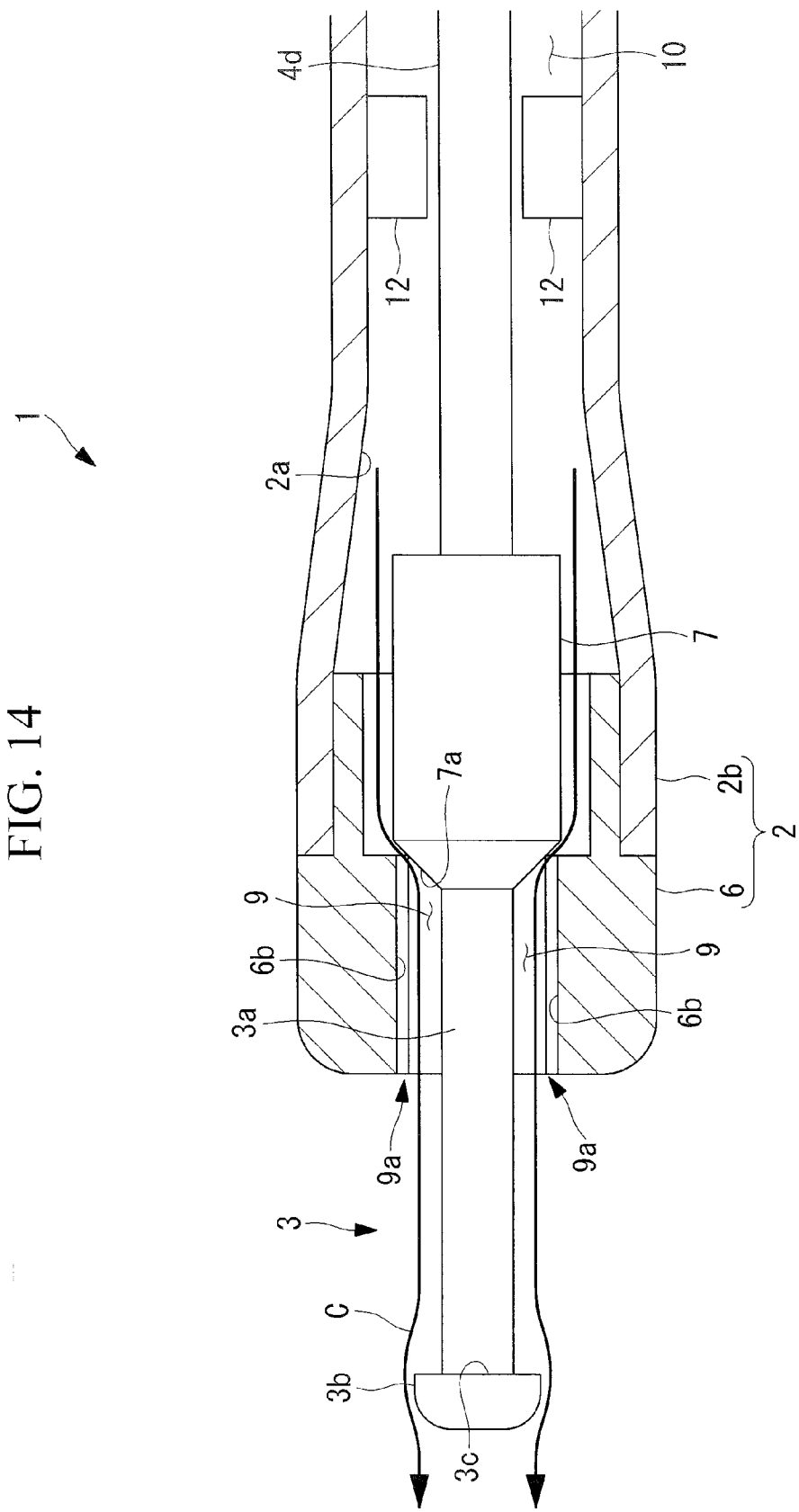
FIG. 14 is a longitudinal sectional view of the vicinity of the distal end of the sheath showing the ninth modification of the high-frequency treatment tool in FIG. 1 in the state in which the electrode member is moved forward.

In addition, as shown in FIG. 14, a distal-end surface 7a of the stopper portion 7 may be formed as a tapered surface so that the electrode member 3 is centered when abutting against the distal-end tip 6.

Figure 16:
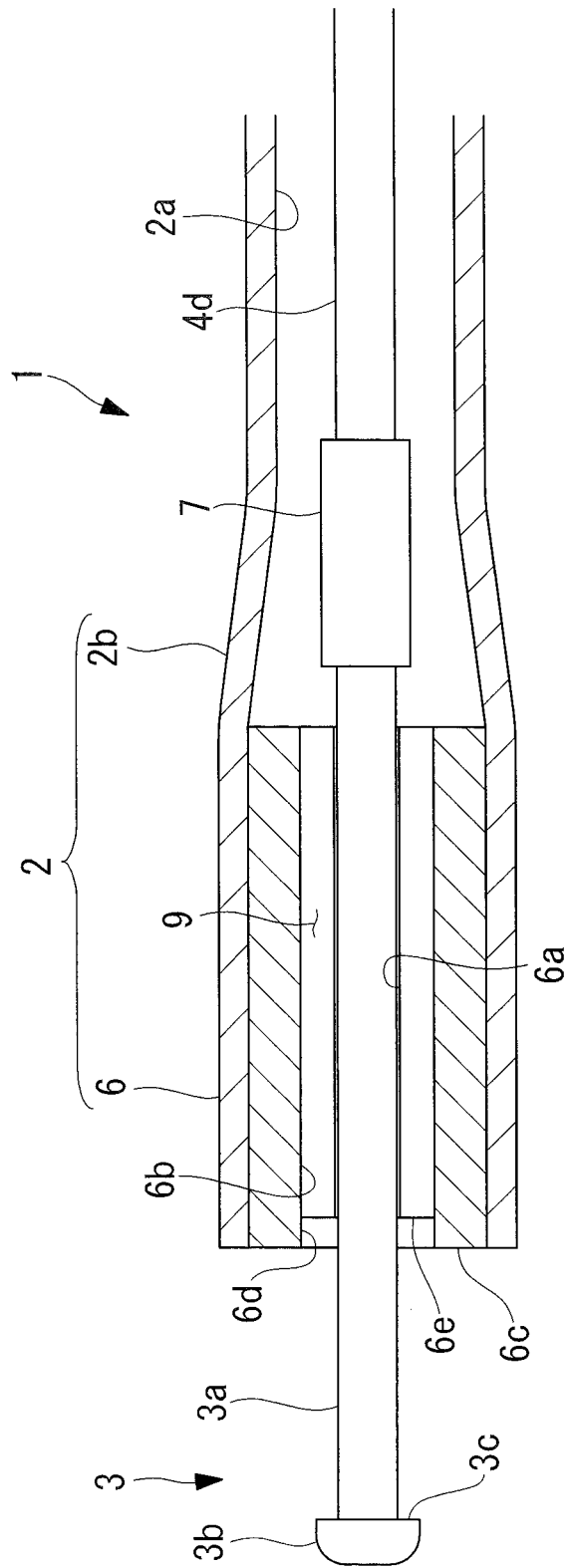
FIG. 16 is a longitudinal sectional view of the vicinity of the distal end of the sheath showing an eleventh modification of the high-frequency treatment tool in FIG. 1, in which a distal-end tip is covered with a tube so that the distal end of the tube and the distal end of the distal-end tip are at substantially the same positions.

In addition, it is permissible to employ a sheath 2 in which the distal-end tip 6 is covered with the tube 2b until the distal end of the tube 2b and the distal end of the distal-end tip 6 come to substantially the same positions, as shown in FIG. 16.

Figure 17A:
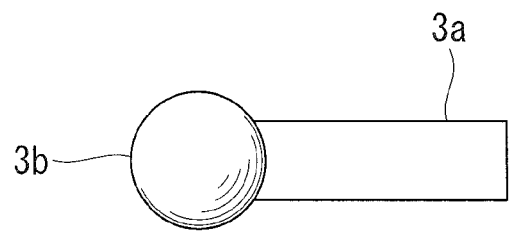
FIG. 17A is a side view of a modification of a distal-end expanded portion of the high-frequency treatment tool in FIG. 1 showing a spherical distal-end expanded portion.
Figure 17B:
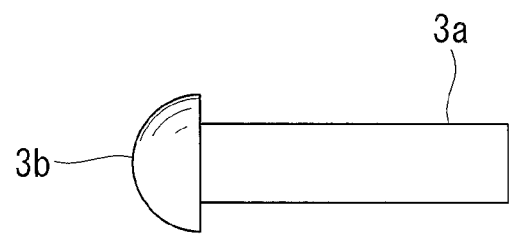
FIG. 17B is a side view of a modification of the distal-end expanded portion of the high-frequency treatment tool in FIG. 1 showing a semispherical distal-end expanded portion.
Figure 17C:
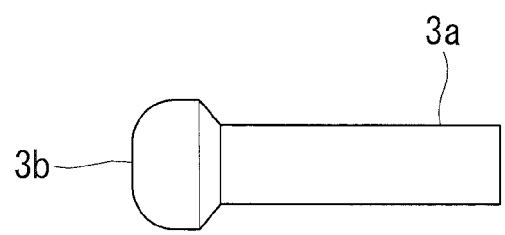
FIG. 17C a side view of a modification of the distal-end expanded portion of the high-frequency treatment tool in FIG. 1 showing a substantially semispherical distal-end expanded portion.
Figure 17D:
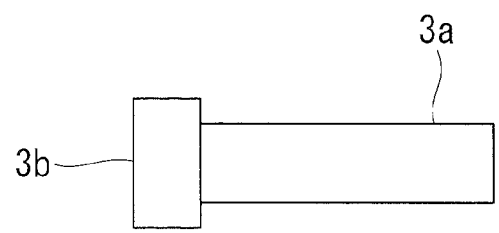
FIG. 17D is a side view of a modification of the distal-end expanded portion of the high-frequency treatment tool in FIG. 1 showing a circular columnar distal-end expanded portion.
Figure 17E:
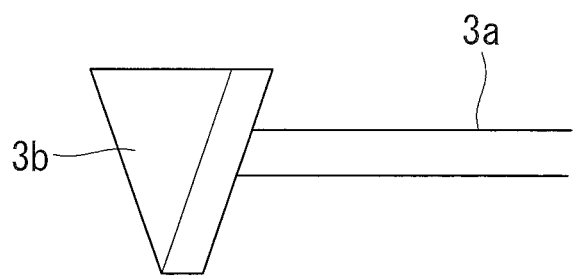
FIG. 17E is a side view of a modification of the distal-end expanded portion of the high-frequency treatment tool in FIG. 1 showing a polygonal plate-like distal-end expanded portion.

In addition, although the distal-end expanded portion 3b has been described as having a substantially discoid shape, the shape thereof is not limited thereto, and the distal-end expanded portion 3b may have an arbitrary shape, such as a spherical shape shown in FIG. 17A, a semispherical shape shown in FIG. 17B, a substantially semispherical shape shown in FIG. 17C, a circular columnar shape shown in FIG. 17D, a polygonal-plate-like shape shown in FIG. 17E or the like, so long as the distal-end expanded portion 3b has a shape that extends in a radiating manner in the direction intersecting the longitudinal direction at least in one portion of the columnar portion 3a in the circumferential direction.

As described above, treatment such as cutting tissue in the body or the like is performed by moving the electrode member forward with respect to the sheath and by supplying a high-frequency current to the electrode member. When cutting or dissecting tissue, by hooking the distal-end expanded portion formed in a radiating manner onto peripheral tissue, it is possible to stably perform treatment without slippage. In addition, by maximally retracting the electrode member until the movement of the electrode member toward the base-end side becomes restricted, only the distal-end expanded portion is exposed at the distal end of the sheath, and thus, even if a high-frequency current is supplied, marking can be performed without making the depth of a cauterizing region deeper than necessary.

Then, in the case in which bleeding occurs in the site in which treatment is being performed, the liquid-feeding unit is activated, the liquid fed via the flow channel provided in the sheath is released from the release port at the distal end of the sheath, and thus, the bleeding site can be washed by releasing the liquid in the vicinity thereof. In this case, when the electrode member is maximally retracted with respect to the sheath, the distal-end expanded portion is at least partially accommodated in the accommodating portion, and, regarding the fluid that has flowed in the flow channel from the base-end side thereof to the distal-end side thereof, the flow of at least a portion of the fluid is blocked by the base-end surface of the distal-end expanded portion, thus flowing radially outward, after which the fluid collides with the inner circumferential surface of the accommodating portion such that the flow thereof is directed in the direction along the longitudinal axis again.

Because there is nothing that blocks the flow of the liquid thereafter, the liquid is released in the longitudinal axial direction. In other words, with this aspect, even in the state in which the electrode member is maximally retracted, it is possible to release the liquid straight ahead in the longitudinal axial direction. As a result, it is possible to locally inject the liquid straight ahead without deeply piercing the electrode member into the tissue more than necessary.

As described above, the abutting portion may be an abutting surface against which the base-end surface of the distal-end expanded portion is abutted.

By doing so, by abutting the base-end surface of the distal-end expanded portion against the abutting surface by retracting the electrode member, regarding the fluid released from the release port, the flow of at least a portion thereof is blocked by the distal-end expanded portion, thus flowing radially outward, after which the fluid is directed by the inner circumferential surface of the accommodating portion in the direction along the longitudinal axis again.

In addition, as described above, the high-frequency treatment tool according to the above-described embodiment may be provided with a sliding hole into which the electrode member is inserted in a movable manner passing through the abutting surface, wherein a portion of the flow channel may be formed between a groove, which is formed in an inner circumferential surface of the sliding hole along a longitudinal direction, and the electrode member, which is disposed in a state in which the electrode member is inserted into the sliding hole, and the groove may extend radially farther outward than the outer circumferential surface of the distal-end expanded portion disposed in a state in which the distal-end expanded portion is inserted into the sliding hole.

By doing so, because the flow of the liquid dispensed from the groove at a portion disposed radially farther outward than the outer circumferential surface of the distal-end expanded portion is unlikely to be blocked by the distal-end expanded portion, the liquid released straight ahead in the longitudinal axial direction can be used to assist release of the liquid blocked by the distal-end expanded portion forward in the longitudinal axial direction.

In addition, as described above, the high-frequency treatment tool according to the above-described embodiment may be provided with a plurality of the grooves in a circumferential direction with spaces therebetween.

By doing so, the liquid can be released from multiple locations in the circumferential direction, and thus, the liquid can be released without causing bias in the circumferential direction.

In addition, as described above, the base-end surface of the distal-end expanded portion may decrease in diameter toward the base-end side thereof and may have a tapered-surface portion that is abutted against an opening of the sliding hole in the abutting surface.

By doing so, when the electrode member is maximally retracted, the tapered-surface portion of the base-end surface of the distal-end expanded portion is abutted against the opening of the sliding hole, and thus, it is possible to align the center axes of the electrode member and the sliding hole in a simple manner. By doing so, it is possible to improve bias in feeding of the liquid.

In addition, as described above, the distal-end expanded portion may have a rotation shape centered on the longitudinal axis, and the abutting surface may be formed of an inclined surface that is inclined from the opening of the sliding hole in an expanding direction toward the distal end and may be abutted against the base-end surface of the distal-end expanded portion at at least three points.

By doing so, when the electrode member is maximally retracted, the base-end surface of the distal-end expanded portion is abutted against the abutting surface formed of the inclined surface at three or more points, and thus, it is possible to set the positions of the electrode member and the sliding hole in a simple manner.

In addition, as described above, the outer circumferential surface of the distal-end expanded portion may be provided with one or more groove portions that is at least partially cut out from the base-end surface in the longitudinal direction.

By doing so, it is possible to increase the amount of fed liquid by increasing the flowing area of the liquid by using the groove portion.

The present invention affords an advantage in that it is possible to release liquid straight ahead even in a state in which an electrode is retracted.

REFERENCE SIGNS LIST 1 high-frequency treatment tool
2 sheath
3 electrode member
3b distal-end expanded portion
3c base-end surface
3e inclined surface (tapered-surface portion)
5 liquid-feeding unit
6a sliding hole
6d accommodating portion
6e bottom surface (abutting surface)
9 flow channel
9a opening
11 groove portion, through-hole

The invention claimed is:
1. A high-frequency treatment tool comprising:
a long, thin cylindrical sheath that is inserted into a body;
an electrode member that is disposed so that the electrode member can be freely made to protrude and be retracted with respect to a distal-end portion of the sheath and to which a high-frequency current is supplied; and
a liquid-feeding unit for feeding a liquid toward a distal-end side of the sheath from a base-end side thereof inside a flow channel formed along a longitudinal axis of the sheath,
wherein a distal end of the electrode member is provided with a distal-end expanded portion that extends radially outward in a radiating manner, that has a base-end surface that is made to protrude and be retracted in the longitudinal axial direction with respect to the distal-end portion of the sheath, and that is formed of a conductive material,
wherein the sheath is provided with:
a tube;
a restricting portion that is connected to a distal end of the tube so as to be positioned forward with respect to the tube, that restricts the movement of the electrode member toward a base-end side at a position at which at least a portion of the distal-end expanded portion is accommodated inside the sheath, and that is formed of an electrically insulating material;
a sliding hole into which the electrode member is inserted in a movable manner passing through the restricting portion and that has a smaller diameter than that of the distal-end expanded portion;
a groove that is formed in an inner circumferential surface of the sliding hole along the longitudinal direction so as to communicate with the sliding hole and that extends radially farther outward than an outer circumferential surface of the distal-end expanded portion in a state in which the distal-end expanded portion is inserted into the sliding hole; and
an accommodating portion that has, at a position farther on the distal-end side than the groove is, an inner circumferential surface that forms a space having a greater diameter than that of the distal-end expanded portion, with which a portion of the distal-end expanded portion can be accommodated inside the sheath,
wherein a portion of the flow channel is formed between the groove and the electrode member, which is disposed so as to allow insertion thereof into the sliding hole,
wherein, in a state in which the distal-end expanded portion is accommodated in the accommodating portion and the movement toward the base-end side is restricted by the restricting portion,
by setting a thickness of the distal-end expanded portion from the base end thereof to the distal end thereof to be greater than a depth of the accommodating portion, a portion of the distal-end expanded portion on the distal-end side thereof is made to protrude from the accommodating portion, and an opening of a ring-shaped release port for releasing the liquid, which is formed between the outer circumferential surface of the distal-end expanded portion and the inner circumferential surface of the accommodating portion, is positioned farther on the base-end side than the distal end of the distal-end expanded portion,
a portion of the groove on the radially inner side is closed by the distal-end expanded portion, and a portion thereof on the radially outer side is exposed without being closed, a liquid fed through the radially inner side of the groove collides with the base-end surface of the distal-end expanded portion and is made to flow radially outward, and the liquid that has collided with the base-end surface of the distal-end expanded portion and that has flowed radially outward collides with the inner circumferential surface of the accommodating portion, thus restoring the flow direction of the liquid to the longitudinal axial direction, and the liquid in which the flow direction thereof has been restored is assisted by a liquid fed through the radially outer side of the groove to flow forward in the longitudinal axial direction, and is released outside the sheath through the release port farther on the base-end side than the distal end of the distal-end expanded portion.

2. A high-frequency treatment tool according to claim 1, wherein the restricting portion has an abutting portion that is provided in the accommodating portion and against which a base-end surface of the distal-end expanded portion is abutted, the inner circumferential surface of the accommodating portion is formed so as to be substantially parallel to the longitudinal axis, at a position at which at least a portion of the distal-end expanded portion is accommodated inside the sheath, the base-end surface of the distal-end expanded portion is abutted against the abutting portion.

3. A high-frequency treatment tool according to claim 2, wherein the abutting portion is an abutting surface against which the base-end surface of the distal-end expanded portion is abutted, and the sliding hole is formed passing through the abutting surface.

4. A high-frequency treatment tool according to claim 1, wherein a plurality of the grooves are provided in a circumferential direction with spaces therebetween.

5. A high-frequency treatment tool according to claim 1, wherein the base-end surface of the distal-end expanded portion decreases in diameter toward the base-end side thereof and has a tapered-surface portion that is abutted against an opening of the sliding hole in the abutting surface.

6. A high-frequency treatment tool according to claim 1, wherein the distal-end expanded portion has a rotation shape centered on the longitudinal axis, and the abutting surface is formed of an inclined surface that is inclined from the opening of the sliding hole in an expanding direction toward the distal end and is abutted against the base-end surface of the distal-end expanded portion at at least three points.

7. A high-frequency treatment tool according to claim 1, wherein the outer circumferential surface of the distal-end expanded portion is provided with one or more groove portions that is at least partially cut out from the base-end surface in the longitudinal direction.

* * * * *